(12) United States Patent
Goldman et al.

(10) Patent No.: US 10,837,971 B2
(45) Date of Patent: Nov. 17, 2020

(54) MASS SPECTROMETRY ASSAY FOR ESTROGENIC COMPOUNDS DURING HORMONE REPLACEMENT THERAPY

(71) Applicant: QUEST DIAGNOSTICS INVESTMENTS INCORPORATED, Wilmington, DE (US)

(72) Inventors: Mildred Goldman, Laguna Niguel, CA (US); Nigel Clarke, Vista, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 0 days.

(21) Appl. No.: 15/251,224

(22) Filed: Aug. 30, 2016

(65) Prior Publication Data

US 2016/0377636 A1 Dec. 29, 2016

Related U.S. Application Data

(63) Continuation of application No. 12/641,227, filed on Dec. 17, 2009, now abandoned.
(Continued)

(51) Int. Cl.
*G01N 33/68* (2006.01)
*G01N 33/74* (2006.01)
(Continued)

(52) U.S. Cl.
CPC ......... *G01N 33/743* (2013.01); *G01N 30/724* (2013.01); *G01N 33/6848* (2013.01);
(Continued)

(58) Field of Classification Search
CPC ........ G01N 33/68; G01N 33/74; G01N 30/72; H01J 49/26
(Continued)

(56) References Cited

U.S. PATENT DOCUMENTS 5,516,528 A 5/1996 Hughes et al.
5,772,874 A 6/1998 Quinn et al.
(Continued)

FOREIGN PATENT DOCUMENTS

WO 0168074 A2 9/2001
WO 2004090525 A1 10/2004

OTHER PUBLICATIONS

Davison, S. et al, Clinical Endocrinology 2003, 58, 249-261.*
(Continued)

*Primary Examiner* — Arlen Soderquist
(74) *Attorney, Agent, or Firm* — Quest Diagnostics, Inc.

(57) ABSTRACT

Methods are provided for detecting the amount of one or more HRT panel analytes (i.e., estrone (E1), estrone sulfate (E1s), 17α-estradiol (E2a), 17β-estradiol (E2b), estradiol sulfate (E2s), estriol (E3), equilin (EQ), 17α-dihydroequilin (EQa), 17β-dihydroequilin (EQb), Equilenin (EN), 17α-dihydroequilenin (ENa), 17β-dihydroequilenin (ENb), and Δ8,9-dehydroestrone (dE1)) in a sample by mass spectrometry. The methods generally involve ionizing one or more HRT panel analytes in a sample and quantifying the generated ions to determine the amount of one or more HRT panel analytes in the sample. In methods where amounts of multiple HRT panel analytes are detected, the amounts of multiple analytes are detected in the same sample injection.

5 Claims, 2 Drawing Sheets

Related U.S. Application Data

(60) Provisional application No. 61/161,160, filed on Mar. 18, 2009, provisional application No. 61/140,575, filed on Dec. 23, 2008.

(51) Int. Cl.
    *H01J 49/26*     (2006.01)
    *G01N 30/72*     (2006.01)
    *H01J 49/00*     (2006.01)

(52) U.S. Cl.
    CPC ...... *G01N 33/6851* (2013.01); *H01J 49/0027* (2013.01); *G01N 2458/15* (2013.01); *H01J 49/00* (2013.01)

(58) Field of Classification Search
    USPC ......... 250/282; 436/119, 127–128, 131, 161, 436/173
    See application file for complete search history.

(56) References Cited

U.S. PATENT DOCUMENTS

| | | | |
|---|---|---|---|
| 5,795,469 | A | 8/1998 | Quinn et al. |
| 5,919,368 | A | 7/1999 | Quinn et al. |
| 5,968,367 | A | 10/1999 | Quinn et al. |
| 6,107,623 | A | 8/2000 | Bateman et al. |
| 6,124,137 | A | 9/2000 | Hutchens et al. |
| 6,204,500 | B1 | 3/2001 | Whitehouse et al. |
| 6,268,144 | B1 | 7/2001 | Koester |
| 6,660,726 | B2 | 12/2003 | Hill et al. |
| 6,855,703 | B1 | 2/2005 | Hill et al. |
| 7,473,560 | B2 | 1/2009 | Soldin |
| 7,618,827 | B2 | 11/2009 | Steven et al. |
| 2002/0151530 | A1* | 10/2002 | Leonard .................. A61P 15/12 514/171 |
| 2003/0083228 | A1* | 5/2003 | Carpino ............... A61K 31/519 514/1 |
| 2004/0186086 | A1 | 9/2004 | Bunschoten et al. |
| 2004/0235193 | A1 | 11/2004 | Soldin |
| 2004/0265916 | A1 | 12/2004 | Dalton et al. |
| 2005/0032758 | A1* | 2/2005 | Rudolph ............... A61K 31/569 514/171 |
| 2007/0004045 | A1 | 1/2007 | Xu et al. |
| 2007/0238713 | A1* | 10/2007 | Gast ........................ A61P 15/00 514/170 |
| 2008/0128606 | A1 | 6/2008 | Grant et al. |
| 2008/0293683 | A1* | 11/2008 | Zhu ........................ A61K 31/56 514/178 |
| 2009/0134325 | A1 | 5/2009 | Goldman et al. |
| 2009/0155766 | A1 | 6/2009 | Goldman et al. |
| 2009/0170823 | A1* | 7/2009 | Diliberti .............. A61K 31/536 514/171 |

OTHER PUBLICATIONS

Draisci, R. et al, Analyst, 1998, 123, 2605-2609.*
Isobe, T. et al, Journal of Chromatography A 2003, 984, 195-202.*
Rodriguez-Mozaz, S. et al, Analytical Chemistry 2004, 76, 6998-7006.*
Beck, I.-C. et al, Journal of Chromatography A 2005,1090, 98-106.*
Johnson, A. C. et al, The Science of the Total Environment 2000, 256, 163-173.*
Croley, T. R. et al, Rapid Communications in Mass Spectrometry 2000, 14, 1087-1093.*
Singh, G. et al, Analytical Chemistry 2000, 72, 3007-3013.*
Valentin-Blasini, L. et al, Journal of Exposure Science and Environmental Epidemiology 2000, 10, 799-807.*
Baronti, C. et al, Environmental Science & Technology 2000, 34, 5059-5066.*
Gentili, A. et al, Chromatographia 2002, 56, 25-32.*
Mitamura, K. et al, Journal of Chromatography B 2000, 748, 89-96.*
Lopez de Alda, M. J. et al, Analyst 2002, 127, 1299-1304.*
Kuster, M. et al, Journal of Hydrology 2008, 358, 112-123.*
Falk, R. T. et al, Cancer Epidemiology, Biomarkers & Prevention 2008, 17, 3411-3418.*
Siekmann L., et al., "Measurement by Isotope Dilution Mass Spectrometry of Equiline and Oestrone in Serum of Women Taking Tablets of Equine Oestrogens," Biomedical Mass Spectrometry, 1983, vol. 10 (3), pp. 168-174.
Soldin O.P., et al., "Steroid Hormone Levels in Pregnancy and 1 Year Postpartum Using Isotope Dilution Tandem Mass Spectrometry," Fertility and Sterility, 2005, vol. 84 (3), pp. 701-710.
Stopforth A., et al., "The Analysis of Estrone and 17beta-Estradiol by Stir Bar Sorptive Extraction-Thermal Desorption-Gas Chromatography/Mass Spectrometry: Application to Urine Samples After Oral Administration of Conjugated Equine Estrogens," Journal of Chromatography B, 2007, vol. 856 (1-2), pp. 156-164.
Sun Y., et al., "Ultrafiltration Tandem Mass Spectrometry of Estrogens for Characterization of Structure and Affinity for Human Estrogen Receptors," Journal of the American Society for Mass Spectrometry, 2005, vol. 16 (2), pp. 271-279.
Supplementary European Search Report for Application No. EP09835643, dated Jul. 19, 2012, 19 pages.
Tai S.S., et al., "Development and Evaluation of a Reference Measurement Procedure for the Determination of Estradiol-17beta in Human Serum Using Isotope-Dilution Liquid Chromatography-Tandem Mass Spectrometry," Analytical Chemistry, 2005, vol. 77 (19), pp. 6359-6363.
Troy S.M., et al., "Differences in Pharmacokinetics and Comparative Bioavailability between Premarin® and Estratab® in Healthy Postmenopausal Women," Current Therapeutic Research, 1994, vol. 55 (4), pp. 359-372.
Wright Jr., G.L., et al., "Proteinchip Surface Enhanced Laser DesorptionIIonization (SELDI) Mass Spectrometry: A Novel Protein Biochip Technology for Detection of Prostate Cancer Biomarkers in Complex Protein Mixtures," Prostate Cancer and Prostatic Diseases, 1999, vol. 2 (5-6), pp. 264-276.
Written Opinion for Application No. PCT/US09/68535, dated Feb. 22, 2010, 5 Pages.
Xu X., et al., "A Liquid Chromatography-Mass Spectrometry Method for the Quantitative Analysis of Urinary Endogenous Estrogen Metabolites," Nature Protocols, 2007, vol. 2 (6), pp. 1350-1355.
Xu X., et al., "Analysis of Fifteen Estrogen Metabolites Using Packed Column Supercritical Fluid Chromatography-Mass Spectrometry," Analytical Chemistry, 2006, vol. 78 (5), pp. 1553-1558.
Xu X., et al., "Measuring Fifteen Endogenous Estrogens Simultaneously in Human Urine by High-Performance Liquid Chromatography-Mass Spectrometry," Analytical Chemistry, 2005, vol. 77 (20), pp. 6646-6654.
Yamamoto A., et al., "Steroid Hormone Profiles of Urban and Tidal Rivers Using LC/MS/MS Equipped with Elextrospray Ionization and Atmospheric Pressure Photoinization Sources," Envrionmental Science and Technology, 2006, vol. 40 (13), pp. 4132-4137.
Yang Y.J., et al., "Direct Determination of Estriol 3- and 16-Glucuronides in Pregnancy Urine by Column-Switching Liquid Chromatography with Electrospray Tandem Mass Spectrometry," Biomedical Chromatography, 2003, vol. 17 (4), pp. 219-225.
Yasui T., et al., "Serum Estrogen Level after Hormone Replacement Therapy and Body Mass Index in Postmenopausal and Bilaterally Ovariectomized Women," Maturitas, 2005, vol. 50 (1), pp. 19-29.
Zhang H., et al., "Quantitative and Qualitative Determination of Estrogen Sulfates in Human Urine by Liquid Chromatography/Tandem Mass Spectrometry Using 96-Well Technology," Analytical Chemistry, 1999, vol. 71 (18), pp. 3955-3964.
Zimmer D., et al., "Comparison of Turbulent-Flow Chromatography with Automated Solid-Phase Extraction in 96-Well Plates and Liquid-Liquid Extraction Used as Plasma Sample Preparation Techniques for Liquid Chromatography-Tandem Mass Spectrometry," Journal of Chromatography A, 1999, vol. 854, pp. 23-35.
Alvarez S., B. et al., "Automated Solid-Phase Extraction for Concentration and Clean-Up of Female Steroid Hormones Prior to Liquid Chromatography-Electrospray Ionization-Tandem Mass Spectrometry: An as Roach to Lipidomics," Journal of Chromatography A, 2008, vol. 1207 (1-2), pp. 46-54.

(56) References Cited

OTHER PUBLICATIONS

Anderson G.L., et al., "Effects of Conjugated Equine Estrogen in Postmenopausal Women with Hysterectomy: The Women's Health Initiative Randomized Controlled Trial," Journal of the American Medical Association, 2004, vol. 291 (14), pp. 1701-1712.

Antignac J.P., et al., "Analytical Strategies for the Direct Mass Spectrometric Analysis of Steroid and Corticosteroid Phase II Metabolites," Steriods, 2005, vol. 70 (3), pp. 205-216.

Arteaga E., et al., "Pharmacokinetic Comparison between Conpremin (Premarin) and a Generic Preparation of Conjugatec Estrogens," Climacteric, 1998, vol. 1 (4), pp. 284-289.

Ayrton J., et al., "The Use of Turbulent Flow Chromatography/Mass Spectrometry for the Rapid, Direct Analysis of a Novel Pharmaceutical Compound in Plasma," Rapid Communications in Mas Spectrometry, 1997, vol. 11, pp. 1953-1958.

Bartolucci G., et al., "Liquid Chromatography Tandem Mass Spectrometric Quantitation of Sulfamethazine and its Metabolites: Direct Analysis of Swine Urine by Triple Quadrupole and by Ion Trap Mass Spectrometry," Rapid Communications in Mass Spectrometry, 2000, vol. 14 (11), pp. 967-973.

Benlhabib E., et al., "Quantitative Analysis of Phytoestrogens in Kudzu-Root, Soy and Spiked Serum Samples by High-Pressure Liquid Chromatography," Biomedical Chromatography, 2004, vol. 18 (6), pp. 367-380.

Bhavnani B.R., et al., "Comparison of Pharmacokinetics of a Conjugated Equine Estrogen Preparation (Premarin) and a Synthetic Mixture of Estrogens (C.E.S.) in Postmenopausal Women," Journal of the Society for Gynecologic Investigation, 2000, vol. 7 (3), pp. 175-183.

Biancotto G., et al., "Determination of 17Beta-Estradiol in Bovine Plasma: Development of a Highly Sensitive Technique by Ion Trap Gas Chromatography-Tandem Mass Spectrometry Using Negative Chemical Ionization," Journal of Mass Spectrometry, 2002, vol. 37 (12), pp. 1266-1271.

Biddle S., et al., "Gas Chromatography-Mass Spectrometry/Mass Spectrometry Analysis to Determine Natural and Post-Administration Levels of Oestrogens in Bovine Serum and Urine," Analytica Chimica Acta, 2007, vol. 586(1-2), pp. 115-121.

Chatman K., et al., "Nanoelectrospray Mass Spectrometry and Precursor Ion Monitoring for Quantitative Steroid Analysis and Attomole Sensitivity," Analytical Chemistry, 1999, vol. 71 (13), pp. 2358-2363.

Chen C.Y., et al., "Determining Estrogenic Steroids in Taipei Waters and Removal in Drinking Water Treatment Using High-Flow Solid-Phase Extraction and Liquid Chromatography/Tandem Mass Spectrometry," Science of the Total Environment, 2007, vol. 378 (3), pp. 352-365.

Chen H.C., et al., "Determination of Estrogenic Compounds in Wastewater Using Liquid Chromatographytandem Mass Spectrometry with Electrospray and Atmospheric Pressure Photoionization Following Desalting Extraction," Chemosphere, 2009, vol. 74 (4), pp. 508-514.

Cohesive Technologies Inc, "Quantification of Steroids from Plasma and/or Serum using Turbulent Flow Chromatography", Chromatography, Sep. 2005, 3 pages.

Curcuruto O., et al., "Investigation of Some Steroids by Means of Thermospray and Tandem Mass-Spectrometry," Rapid Communications in Mass Spectrometry, 1993, vol. (7) 7, pp. 673-675.

Deng Y., et al., "Tandem Mass Spectrometry with Online High-Flow Reversed-Phase Extraction and Normal-Phase Chromatography on Silica Columns with Aqueous-Organic Mobile Phase for Quantitation of Polar Compounds in Biological Fluids," Rapid Communications in Mass Spectrometry, 2005, vol. 19 (20), pp. 2929-2934.

Diaz-Cruz M.S., et al., "Determination of Estrogens and Progestogens by Mass Spectrometric Techniques (GC/MS, LC/MS and LC/MS/MS)," Journal of Mass Spectrometry, 2003, vol. 38 (9), pp. 917-923.

Dorgan A.F., et al., "Measurement of Steroid Sex Hormones in Serum: A Comparison of Radioimmunoassay and Mass Spectrometry," Steroids, 2002, vol. 67 (3-4), pp. 151-158.

Draisci R., et al., "Confirmation of Anabolic Hormone Residues in Bovine Blood by Micro-HPLC-Ion Spray-Tandem Mass Spectrometry," Journal of High Resolution Chromatography, 1997, vol. 20 (8), pp. 421-426.

Extended European Search Report for Application No. 09835643.9, dated Jul. 19, 2012.

Fedeniuk R.W. et al., "Validation of a Gas Chromatography-Mass Spectrometry Method for the Determination of Pg/MI Levels of 17Beta-Estradiol and 17 Beta-Trenbolone in Bovine Serum," Journal of Chromatography B, 2004, vol. 802 (2), pp. 307-315.

Ferguson P. L., et al., "Determination of Steroid Estrogens in Wastewater by Immunoaffinity Extraction Coupled with HPLC-Electrospray-MS," Analytical Chemistry, 2001, vol. 73 (16), pp. 3890-3895.

Final Office Action dated Aug. 6, 2013 for U.S. Appl. No. 12/641,227, filed Dec. 17, 2009.

Final Office Action dated Jun. 13, 2012 for U.S. Appl. No. 12/641,227, filed Dec. 17, 2009.

Guo T., et al., "Simultaneous Determination of 12 Steroids by Isotope Dilution Liquid Chromatography-Photospray Ionization Tandem Mass Spectrometry," Analytica Chimica Acta, 2006, vol. 372 (1-2), pp. 76-82.

Guo T., et al., "Rapid Measurement of Estrogens and their Metabolites in Human Serum by Liquid Chromatography-Tandem Mass Spectrometry without Derivatization," Clinical Biochemistry, 2008, vol. 41 (9), pp. 736-741.

Guo T., et al., "Steroid Profiles Using Liquid Chromatography-Tandem Mass Spectrometry with Atmospheric Pressure Photoionization Source," Archives of Pathology & Laboratory Medicine, 2004, vol. 128 (4), pp. 469-475.

Ikegawa S., et al., "Immunoaffinity Extraction for Liquid Chromatographic Determination of Equilin and Its Metabolites in Plasma," Biomedical Chromatography, 1996, vol. 10 (2), pp. 73-77.

International Search Report and Written Opinion for Application No. PCT/US2009/068535, dated Feb. 22, 2010.

International Search Report for Application No. PCT/US09/68535, dated Feb. 22, 2010, 3 Pages.

Kauppila T.J., et al., "Atmospheric Pressure Photoionization-Mass Spectrometry and Atmospheric Pressure Chemical Ionization-Mass Spectrometry of Neurotransmitters," Journal of Mass Spectrometry, 2006, vol. 41 (6), pp. 781-789.

Lagana A., et al., "Trace Analysis of Estrogenic Chemicals in Sewage Effluent Using Liquid Chromatography Combined With Tandem Mass Spectrometry," Rapid Communications in Mass Spectrometry, 2000, vol. 14 (6), pp. 401-407.

Leung Y.S , et al., "Falsely Increased Serum Estradiol Results Reported in Direct Estradiol Assays," Clinical Chemistry, 1997, vol. 43 (7), pp. 1250-1251.

Mazzarino M., et al., "A Fast Liquid Chromatographic/Mass Spectrometric Screening Method for the Simultaneous Detection of Synthetic Glucocorticoids, Some Stimulants, Anti-Oestrogen Drugs and Synthetic Anabolic Steroids," Rapid Communications in Mass Spectrometry, 2006, vol. 20 (22), pp. 3465-3476.

Mellon-Nussbaum S.M., et al., "Estradiol Fatty Acid Esters. The Isolation and Identification of the Lipoidal Derivative of Estradiol Synthesized in the Bovine Uterus," The Journal of Biological Chemistry, 1982, vol. 257 (10), pp. 5678-5684.

Merchant M., et al., "Recent Advancements in Surface-Enhanced Laser DesorptionIIonization-Time of Flight-Mass Spectrometry," Electrophoresis, 2000, vol. 21 (6), pp. 1164-1167.

Nachtigall L.E., et al., "Serum Estradiol-Binding Profiles in Postmenopausal Women Undergoing Three Common Estrogen Replacement Therapies: Associations with Sex Hormone-Binding globulin, Estradiol, and Estrone Levels," Menopause, 2000, vol. 7 (4), pp. 243-250.

Nelson R.E., et al., "Liquid Chromatography-Tandem Mass Spectrometry Assay for Simultaneous Measurement of Estradiol and Estrone in Human Plasma," Clinical Chemistry, 2004, vol. 50 (2), pp. 373-384.

Nielen M.W.F., et al.,"Bioassay-Directed Identification of Estrogen Residues in Urine by Liquid Chromatography Electrospray Quadrupole Time-of-Flight Mass Spectrometry," Analytical Chemistry, 2004, vol. 76 (22), pp. 6600-6608.

(56) References Cited

OTHER PUBLICATIONS

Non-Final Office Action dated Mar. 20, 2013 for U.S. Appl. No. 12/641,227, filed Dec. 17, 2009.
Non-Final Office Action dated Jan. 22, 2016 for U.S. Appl. No. 14/063,956, filed Oct. 25, 2013.
Non-Final Office Action dated Oct. 28, 2011 for U.S. Appl. No. 12/641,227, filed Dec. 17, 2009.
Non-Final Office Action dated Mar. 31, 2011 for U.S. Appl. No. 12/641,227, filed Dec. 17, 2009.
Pasqualini J.R., et al., "Concentrations of Estrone, Estradiol, and Estrone Sulfate and Evaluation of Sulfatase and Aromatase Activities in Pre- and Postmenopausal Breast Cancer Patients," The Journal of Clinical Endocrinology and Metabolism, 1996, vol. 81 (4), pp. 1460-1464.
Patent Board Decision—Examiner Affirmed dated Jun. 30, 2016 for U.S. Appl. No. 12/614,227, filed Dec. 17, 2009.
Qin F., et al., "Hydrophilic Interaction Liquid Chromatography-Tandem Mass Spectrometry Determination of Estrogen Conjugates in Human Urine," Analytical Chemistry, 2008, vol. 80 (9), pp. 3404-3411.
Reepmeyer J.C., et al., "Separation and Detection of the Isomeric Equine Conjugated Estrogens, Equilin Sulfate and Delta-Dehydroestrone Sulfate, by Liquid Chromatography-Electrospray-Mass Spectrometry Using Carbon-Coated Zirconia and Porous Graphitic Carbon Stationary Phases," Journal of Chromatography, 2005, vol. 1083 (1-2), pp. 42-51.
Robb D.B., et al., "Atmospheric Pressure Photoionization: An Ionization Method for Liquid Chromatography—Mass Spectrometry," Analytical Chemistry, 2000, vol. 72 (15), pp. 3653-3659.
Rossouw J.E., et al., "Risks and Benefits of Estrogen plus Progestin in Healthy Postmenopausal Women: Principal Results from the Women's Health Initiative Randomized Controlled Trial," Journal of the American Medical Association, 2002, vol. 288 (3), pp. 321-331.
Santen R.J., et al., "Superiority of Gas Chromatography/Tandem Mass Spectrometry Assay (GC/MS/MS) for Estradiol for Monitoring of Aromatase Inhibitor Therapy," Steroids, 2007, vol. 72 (8), pp. 666-671.
Lopez de Alda, M., et al., "Liquid Chromatography-(tandem) Mass Spectrometry of Selected Emergin Pollutants . . . ," J Chromatogr, 2003, A 1000, pp. 503-526.

\* cited by examiner

MASS SPECTROMETRY ASSAY FOR ESTROGENIC COMPOUNDS DURING HORMONE REPLACEMENT THERAPY

CROSS REFERENCE TO RELATED PATENT APPLICATIONS

This application is a continuation application of U.S. application Ser. No. 12/641,227, filed Dec. 17, 2009, now abandoned, which claims priority to U.S. application. No. 61/161,160, filed Mar. 18, 2009, and U.S. application. No. 61/140,575, filed Dec. 23, 2008, each of which is hereby incorporated by reference in its entirety.

FIELD OF THE INVENTION

The invention relates to methods for measurement of certain estrogenic compounds, in particular by tandem mass spectrometry.

BACKGROUND OF THE INVENTION

The following description of the background of the invention is provided simply as an aid in understanding the invention and is not admitted to describe or constitute prior art to the invention.

Hormone replacement therapy (HRT) is a treatment to artificially boost the hormone levels for surgically menopausal, perimenopausal and postmenopausal women. The main hormones involved in HRT are estrogens, progestins and sometimes testosterone. They can be delivered to the body via patches, tablets, creams, gels, troches, IUDs, and injections (rarely) in dosages of sequentially combined HRT (scHRT) or continuous combined HRT (ccHRT). HRT is also useful for treatment of menopausal symptoms.

The most commonly and widely prescribed form of HRT is Premarin®. Premarin® is a compound drug consisting of 10 biologically active estrogens or conjugated equine estrogens (estrone (E1), equilin (EQ), 17α-dihydroequilin (EQa), 17α-estradiol (E2a), 17β-dihydroequilin (EQb), 17α-dihydroequilenin (ENa), 17β-dihydroequilenin (ENb), equilenin (EN), 17β-estradiol (E2b), Δ8,9-dehydroestrone (dE1), and conjugates thereof). These estrogens are present mainly as "conjugates," i.e., modified chemical forms in which the active estrogen is coupled to another chemical group such as sulfate. After being taken into the woman's body, the conjugated estrogens of Premarin® are converted to the active unconjugated estrogens or excreted from the woman's body. A number of clinical trials have confirmed the effectiveness of HRT in preserving and increasing bone mineral density in postmenopausal women.

However, a link between estrogens and various increased health risks, such as developing breast cancer or various cardiovascular conditions, has been reported. See The Women's Health Initiative Steering Committee, *JAMA* 2004, 14:1701-12; and The Writing Group for the Women's Health Initiative Investigators, *JAMA* 2002, 3:321-333.

Previously, methods have been reported for measuring various estrogens affected by HRT. For example, Goldman, et al., U.S. patent application Ser. Nos. 11/946, 017, 12/002, 314, and 12/328,735, describe measurement of estradiol and estrone by mass spectrometry techniques; Chen, H. C., et al., *Chemosphere* 2008, Epub ahead of print; and Alavarez, S., et al., *J. Chromatogr A* 2008, 1201:46-54 report measuring estrone, estradiol, and estriol using liquid chromatography tandem mass spectrometry in wastewater samples and urine, respectively. Qin, F., et al., Anal Chem. 2008, 80:3404-11, reported hydrophilic interaction liquid chromatography with tandem mass spectrometry for detection of urinary estrogen conjugates. Reepmeyer, J. C., et al., *J. Chromatogr A* 2005, 1083:42-51, reported detection of equilin-3-sulfate and Δ8,9-dehydroestrone-3-sulfate by liquid chromatography tandem mass spectrometry using carbon-coated zirconia and porous graphitic carbon stationary phases.

SUMMARY OF THE INVENTION

Methods are provided for detecting the amount of one or more (and preferably multiple) HRT panel analytes (i.e., estrone (E1), estrone sulfate (E1s), 17α-estradiol (E2a), 17β-estradiol (E2b), estradiol sulfate (E2s), estriol (E3), equilin (EQ), 17α-dihydroequilin (EQa), 17β-dihydroequilin (EQb), Equilenin (EN), 17α-dihydroequilenin (ENa), 17β-dihydroequilenin (ENb), and Δ8,9-dehydroestrone (dE1)) in a sample by mass spectrometry, including tandem mass spectrometry. In methods where amounts of multiple HRT panel analytes are detected, the amounts of multiple analytes are detected in the same sample injection.

These methods include: subjecting a sample, purified by methods described below, to ionization under conditions suitable to produce one or more ions detectable by mass spectrometry from each of one or more HRT panel analytes; determining the amounts of one or more ions from each of the one or more HRT panel analytes by tandem mass spectrometry; and using the amounts of the one or more ions from each of the one or more HRT panel analytes to determine the amounts of each of the one or more HRT panel analytes in the sample. Preferably, the sample is a biological fluid; more preferably the sample is serum.

Some embodiments presented herein may be useful for determining the level of two or more circulating estrogenic compounds in an individual undergoing hormone replacement therapy (HRT). In related embodiments, a ratio may be calculated between the levels of two or more circulating estrogenic compounds in an individual. In these embodiments, the ratio is a comparison of the combined levels of one or more sulfated estrogenic compounds and the combined levels of one or more non-sulfated estrogenic compounds. In these embodiments, the predominance of the non-sulfated form may indicate that a decrease in the individual's HRT dosage may be desirable. Alternatively, if the sulfated form is predominant, an increase in the individual's HRT dosage may be desirable. In certain preferred embodiments, the non-sulfated estrogenic compound(s) comprise the non-sulfated versions of the sulfated estrogenic compound(s). In these embodiments, the one or more sulfated estrogenic compounds comprise one or more estrogenic compounds selected from the group consisting of estrone sulfate (E1s) and estradiol sulfate (E2s).

In preferred embodiments, the amounts of two or more, three or more, four or more, five or more, six or more, seven or more, eight or more, nine or more, ten or more, eleven or more, twelve or more, or thirteen or more HRT panel analytes are determined.

In embodiments where only one HRT panel analyte or estrogenic compound is determined, the HRT panel analyte or estrogenic compound excludes E1. In some embodiments where only two HRT panel analytes or estrogenic compounds are determined, the two HRT panel analytes or estrogenic compounds exclude the combination of E1 and E3 or the combination of E1S and E2S. In some embodiments where only three HRT panel analytes or estrogenic compounds are determined, the three HRT panel analytes or estrogenic compounds exclude the combination of E1, E2b and E3. In embodiments where the sample is subjected to turbulent flow liquid chromatography prior to ionization, the specific combinations indicated above of two or three HRT panel analytes or estrogenic compounds may not be excluded. All of the above embodiments apply to detection of estrogenic compounds in an sample including where the sample is taken from an individual undergoing hormone replacement therapy.

In some embodiments, one of the one or more HRT panel analytes is E1. In related embodiments, one or more ions from E1 comprise ions selected from the group consisting of negative ions with a mass to charge ratio (m/z) of 269.10±0.50, 145.10±0.50, and 143.09±0.50. In particularly preferred embodiments, one or more ions from E1 comprise a precursor ion with m/z of 269.10±0.50, and one or more fragment ions selected from the group of ions with m/z of 145.10±0.50 and 143.09±0.50.

In some embodiments, one of the one or more HRT panel analytes is E1s. In related embodiments, one or more ions from E1s comprise ions selected from the group consisting of negative ions with a mass to charge ratio (m/z) of 349.01±0.50, 145.10±0.50, and 143.08±0.50. In particularly preferred embodiments, one or more ions from E1s comprise a precursor ion with m/z of 349.01±0.50, and one or more fragment ions selected from the group of ions with m/z of 145.10±0.50 and 143.08±0.50.

In some embodiments, one of the one or more HRT panel analytes is E2a. In related embodiments, one or more ions from E2a comprise ions selected from the group consisting of negative ions with a mass to charge ratio (m/z) of 271.12±0.50, 145.10±0.50, and 143.1±0.50. In particularly preferred embodiments, one or more ions from E2a comprise a precursor ion with m/z of 271.12±0.50, and one or more fragment ions selected from the group of ions with m/z of 145.10±0.50 and 143.1±0.50.

In some embodiments, one of the one or more HRT panel analytes is E2b. In related embodiments, one or more ions from E2b comprise ions selected from the group consisting of negative ions with a mass to charge ratio (m/z) of 271.12±0.50, 183.10±0.50, and 169.10. In particularly preferred embodiments, one or more ions from E2b comprise a precursor ion with m/z of 271.12±0.50, and one or more fragment ions selected from the group of ions with m/z of 183.10±0.50 and 169.10.

In some embodiments, one of the one or more HRT panel analytes is E2s. In related embodiments, one or more ions from E2s comprise ions selected from the group consisting of negative ions with a mass to charge ratio (m/z) of 351.02±0.50, 183.10±0.50, and 145.10±0.50. In particularly preferred embodiments, one or more ions from E2s comprise a precursor ion with m/z of 351.02±0.50, and one or more fragment ions selected from the group of ions with m/z of 183.10±0.50 and 145.10±0.50.

In some embodiments, one of the one or more HRT panel analytes is E3. In related embodiments, one or more ions from E3 comprise ions selected from the group consisting of negative ions with a mass to charge ratio (m/z) of 287.10±0.50, 171.10±0.50, and 143.10±0.50. In particularly preferred embodiments, one or more ions from E3 comprise a precursor ion with m/z of 287.10±0.50, and one or more fragment ions selected from the group of ions with m/z of 171.10±0.50 and 143.10±0.50.

In some embodiments, one of the one or more HRT panel analytes is EQ. In related embodiments, one or more ions from EQ comprise ions selected from the group consisting of negative ions with a mass to charge ratio (m/z) of 267.06±0.50, 181.07±0.50, and 115.07±0.50. In particularly preferred embodiments, one or more ions from EQ comprise a precursor ion with m/z of 267.06±0.50, and one or more fragment ions selected from the group of ions with m/z of 181.07±0.50 and 115.07±0.50.

In some embodiments, one of the one or more HRT panel analytes is EQa. In related embodiments, one or more ions from EQa comprise ions selected from the group consisting of negative ions with a mass to charge ratio (m/z) of 269.10±0.50, 183.11±0.50, and 169.10±0.50. In particularly preferred embodiments, one or more ions from EQa comprise a precursor ion with m/z of 269.10±0.50, and one or more fragment ions selected from the group of ions with m/z of 183.11±0.50 and 169.10±0.50.

In some embodiments, one of the one or more HRT panel analytes is EQb. In related embodiments, one or more ions from EQb comprise ions selected from the group consisting of negative ions with a mass to charge ratio (m/z) of 269.09±0.50, 193.10±0.50, and 143.10±0.50. In particularly preferred embodiments, one or more ions from EQb comprise a precursor ion with m/z of 269.09±0.50, and one or more fragment ions selected from the group of ions with m/z of 193.10±0.50 and 143.10±0.50.

In some embodiments, one of the one or more HRT panel analytes is EN. In related embodiments, one or more ions from EN comprise ions selected from the group consisting of negative ions with a mass to charge ratio (m/z) of 265.09±0.50, 221.08±0.50, and 193.10±0.50. In particularly preferred embodiments, one or more ions from EN comprise a precursor ion with m/z of 265.09±0.50, and one or more fragment ions selected from the group of ions with m/z of 221.08±0.50 and 193.10±0.50.

In some embodiments, one of the one or more HRT panel analytes is ENa. In related embodiments, one or more ions from ENa comprise ions selected from the group consisting of negative ions with a mass to charge ratio (m/z) of 267.08±0.50, 195.13±0.50, and 180.10±0.50. In particularly preferred embodiments, one or more ions from ENa comprise a precursor ion with m/z of 267.08±0.50, and one or more fragment ions selected from the group of ions with m/z of 195.13±0.50 and 180.10±0.50.

In some embodiments, one of the one or more HRT panel analytes is ENb. In related embodiments, one or more ions from ENb comprise ions selected from the group consisting of negative ions with a mass to charge ratio (m/z) of 267.08±0.50, 195.12±0.50, and 180.09±0.50. In particularly preferred embodiments, one or more ions from ENb comprise a precursor ion with m/z of 267.08±0.50, and one or more fragment ions are selected from the group of ions with m/z of 195.12±0.50 and 180.09±0.50.

In some embodiments, one of the one or more HRT panel analytes is dE1. In related embodiments, one or more ions from dE1 comprise ions selected from the group consisting of negative ions with a mass to charge ratio (m/z) of 267.06±0.50, 195.08±0.50, and 171.07±0.50. In particularly preferred embodiments, one or more ions from dE1 comprise a precursor ion with m/z of 267.06±0.50, and one or more fragment ions selected from the group of ions with m/z of 195.08±0.50 and 171.07±0.50.

Embodiments of the present invention may involve the combination of liquid chromatography with mass spectrometry. In some embodiments, the liquid chromatography may comprise HPLC, UPLC, TFLC, or any combination thereof. For example, in some embodiments, HPLC, alone or in combination with one or more purification methods such as for example SPE (e.g., TFLC) and/or protein precipitation and filtration, is utilized to purify an analyte in a sample. In other embodiments, the liquid chromatography may comprise UPLC, either alone or in combination with one or more additional purification methods, such as SPE (e.g., TFLC) and/or protein precipitation and filtration, to purify an analyte in a sample.

As used herein, hormone replacement therapy (HRT) is a treatment to artificially boost the reproductive hormone levels in women undergoing treatment. The main reproductive hormones involved in HRT are estrogens, progestins and sometimes testosterone. They can be delivered to the body via patches, tablets, creams, gels, troches, IUDs, and injections (rarely) in dosages of sequentially combined HRT (scHRT) or continuous combined HRT (ccHRT).

In some embodiments, at least one purification step and mass spectrometric analysis is conducted in an on-line fashion. In another preferred embodiment, the mass spectrometry is tandem mass spectrometry (MS/MS).

In certain preferred embodiments of the methods disclosed herein, mass spectrometry is performed in negative ion mode. Alternatively, mass spectrometry is performed in positive ion mode. Various ionization sources, including for example atmospheric pressure chemical ionization (APCI) or electrospray ionization (ESI), may be used in embodiments of the present invention. In certain preferred embodiments, one or more estrogenic compounds and/or internal standards are ionized using heated ESI in negative ion mode.

In preferred embodiments, one or more separately detectable internal standards is provided in the sample, the amount of which is also determined in the sample. In these embodiments, all or a portion of one or more endogenous analytes selected from the group consisting of HRT panel analytes, and the one or more internal standards present in the sample are ionized to produce a plurality of ions detectable in a mass spectrometer. In preferred embodiments, the amount of ions generated from an analyte of interest may be related to the presence of amount of analyte of interest in the sample by comparison to one or more internal standards.

Preferred internal standards include $d_4$-estrone (E1-d4), $d_2$-17α-estradiol (E2a-d2), $d_5$-17β-estradiol (E2b-d5), $d_3$-estriol (E3-d3), $d_4$-equilin (EQ-d4), $d_5$-17β-dihydroequilin (EQb-d5), $d_3$-equilenin (EN-d3), $d_3$-17β-dihydroequilenin (ENb-d3), $d_4$-estrone sulfate (E1s-d4), $d_4$-17β-estradiol sulfate (E2bs-d4), and $d_2$-Δ8,9-dehydroestrone (dE1-d2). However, this listing of preferred internal standards is not intended to be exclusive, i.e., other suitable internal standards may be used.

In preferred embodiments, E1-d4 ions detectable in a mass spectrometer are selected from the group consisting of positive ions with a mass to charge ratio (m/z) of 273.13±0.50, and 147.08±0.50. In particularly preferred embodiments, E1-d4 ions comprise a precursor ion with m/z of 273.13±0.50, and a fragment ion with m/z of 147.08±0.50.

In preferred embodiments, E2a-d2 ions detectable in a mass spectrometer are selected from the group consisting of positive ions with a mass to charge ratio (m/z) of 273.20±0.50, and 147.08±0.50. In particularly preferred embodiments, E2a-d2 ions comprise a precursor ion with m/z of 273.20±0.50, and a fragment ion with m/z of 147.08±0.50.

In preferred embodiments, E2b-d5 ions detectable in a mass spectrometer are selected from the group consisting of positive ions with a mass to charge ratio (m/z) of 276.13±0.50, and 187.08±0.50. In particularly preferred embodiments, E2b-d5 ions comprise a precursor ion with m/z of 276.13±0.50, and a fragment ion with m/z of 187.08±0.50.

In preferred embodiments, E3-d3 ions detectable in a mass spectrometer are selected from the group consisting of positive ions with a mass to charge ratio (m/z) of 290.20±0.50, and 173.10±0.50. In particularly preferred embodiments, E3-d3 ions comprise a precursor ion with m/z of 290.20±0.50, and a fragment ion with m/z of 173.10±0.50.

In preferred embodiments, EQ-d4 ions detectable in a mass spectrometer are selected from the group consisting of positive ions with a mass to charge ratio (m/z) of 271.16±0.50, and 243.14±0.50. In particularly preferred embodiments, EQ-d4 ions comprise a precursor ion with m/z of 271.16±0.50, and a fragment ion with m/z of 243.14±0.50.

In preferred embodiments, EQb-d5 ions detectable in a mass spectrometer are selected from the group consisting of positive ions with a mass to charge ratio (m/z) of 274.15±0.50, and 213.10±0.50. In particularly preferred embodiments, EQb-d5 ions comprise a precursor ion with m/z of 274.15±0.50, and a fragment ion with m/z of 213.10±0.50.

In preferred embodiments, EN-d3 ions detectable in a mass spectrometer are selected from the group consisting of positive ions with a mass to charge ratio (m/z) of 268.15±0.50, and 182.08±0.50. In particularly preferred embodiments, EN-d3 ions comprise a precursor ion with m/z of 268.15±0.50, and a fragment ion with m/z of 182.08±0.50.

In preferred embodiments, ENb-d3 ions detectable in a mass spectrometer are selected from the group consisting of positive ions with a mass to charge ratio (m/z) of 270.17±0.50, and 182.08±0.50. In particularly preferred embodiments, ENb-d3 ions comprise a precursor ion with m/z of 270.17±0.50, and a fragment ion with m/z of 182.08±0.50.

In preferred embodiments, E1s-d4 ions detectable in a mass spectrometer are selected from the group consisting of positive ions with a mass to charge ratio (m/z) of 352.9±0.50, and 147.09±0.50. In particularly preferred embodiments, E1s-d4 ions comprise a precursor ion with m/z of 352.9±0.50, and a fragment ion with m/z of 147.09±0.50.

In preferred embodiments, E2bs-d4 ions detectable in a mass spectrometer are selected from the group consisting of positive ions with a mass to charge ratio (m/z) of 355.0±0.50, and 275.18±0.50. In particularly preferred embodiments, E2bs-d4 ions comprise a precursor ion with m/z of 355.0±0.50, and a fragment ion with m/z of 275.18±0.50.

In preferred embodiments, dE1-d2 ions detectable in a mass spectrometer are selected from the group consisting of positive ions with a mass to charge ratio (m/z) of 269.02±0.50, and 209.05±0.50. In particularly preferred embodiments, dE1-d2 ions comprise a precursor ion with m/z of 269.02±0.50, and a fragment ion with m/z of 209.05±0.50.

In other embodiments, the amount of an analyte in a sample may be determined by comparison of the amount of one or more analyte ions detected by mass spectrometry to the amount of one or more standard ions detected by mass spectrometry in an external reference standard. Exemplary external reference standards may comprise blank plasma or serum spiked with a known amount of one or more of the above named internal standards and/or analytes of interest.

The features of the embodiments listed above may be combined without limitation for use in methods of the present invention.

As used herein, unless otherwise stated, the singular forms "a," "an," and "the" include plural reference. Thus, for example, a reference to "a protein" includes a plurality of protein molecules.

As used herein, an "isotopic label" produces a mass shift in the labeled molecule relative to the unlabeled molecule when analyzed by mass spectrometric techniques. Examples of suitable labels include deuterium, $^{13}C$, and $^{15}N$. Deuterium is a useful label because it can potentially produce three mass unit shifts in a labeled methylation product relative to an unlabeled methylation product. For example, $d_4$-estrone has a mass four units higher than estrone. The iosotopic label can be incorporated at one or more positions in the molecule and one or more kinds of isotopic labels can be used on the same isotopically labeled molecule.

As used herein, the term "purification" or "purifying" does not refer to removing all materials from the sample other than the analyte(s) of interest. Instead, purification refers to a procedure that enriches the amount of one or more analytes of interest relative to other components in the sample that may interfere with detection of the analyte of interest. Purification of the sample by various means may allow relative reduction of one or more interfering substances, e.g., one or more substances that may or may not interfere with the detection of selected parent or daughter ions by mass spectrometry. Relative reduction as this term is used does not require that any substance, present with the analyte of interest in the material to be purified, is entirely removed by purification.

As used herein, the term "sample" refers to any sample that may contain an analyte of interest. As used herein, the term "body fluid" means any fluid that can be isolated from the body of an individual. For example, "body fluid" may include blood, plasma, serum, bile, saliva, urine, tears, perspiration, and the like. Preferred samples for use in the present invention comprise human serum and human plasma. Such samples derived from an individual undergoing hormone replacement therapy, particularly serum or plasma, are useful for determining the level of circulating estrogenic compounds in the individual.

As used herein, the term "solid phase extraction" or "SPE" refers to a process in which a chemical mixture is separated into components as a result of the affinity of components dissolved or suspended in a solution (i.e., mobile phase) for a solid through or around which the solution is passed (i.e., solid phase). In some instances, as the mobile phase passes through or around the solid phase, undesired components of the mobile phase may be retained by the solid phase resulting in a purification of the analyte in the mobile phase. In other instances, the analyte may be retained by the solid phase, allowing undesired components of the mobile phase to pass through or around the solid phase. In these instances, a second mobile phase is then used to elute the retained analyte off of the solid phase for further processing or analysis.

As used herein, the term "chromatography" refers to a process in which a chemical mixture carried by a liquid or gas is separated into components as a result of differential distribution of the chemical entities as they flow around or over a stationary liquid or solid phase.

As used herein, the term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Examples of "liquid chromatography" include reverse phase liquid chromatography (RPLC), high performance liquid chromatography (HPLC), and turbulent flow liquid chromatography (TFLC) (sometimes known as high turbulence liquid chromatography (HTLC) or high throughput liquid chromatography).

As used herein, the term "high performance liquid chromatography" or "HPLC" (also sometimes known as "high pressure liquid chromatography") refers to liquid chromatography in which the degree of separation is increased by forcing the mobile phase under pressure through a stationary phase, typically a densely packed column. As used herein, the term "ultra high performance liquid chromatography" or "UPLC" or "UHPLC" (sometimes known as "ultra high pressure liquid chromatography") refers to HPLC which occurs at much higher pressures than traditional HPLC techniques.

As used herein, the term "turbulent flow liquid chromatography" or "TFLC" (sometimes known as high turbulence liquid chromatography or high throughput liquid chromatography) refers to a form of chromatography that utilizes turbulent flow of the material being assayed through the column packing as the basis for performing the separation. TFLC has been applied in the preparation of samples containing two unnamed drugs prior to analysis by mass spectrometry. See, e.g., Zimmer et al., *J Chromatogr A* 854: 23-35 (1999); see also, U.S. Pat. Nos. 5,968,367, 5,919,368, 5,795,469, and 5,772,874, which further explain TFLC. Persons of ordinary skill in the art understand "turbulent flow." When fluid flows slowly and smoothly, the flow is called "laminar flow." For example, fluid moving through an HPLC column at low flow rates is laminar. In laminar flow the motion of the particles of fluid is orderly with particles moving generally in straight lines. At faster velocities, the inertia of the water overcomes fluid frictional forces and turbulent flow results. Fluid not in contact with the irregular boundary "outruns" that which is slowed by friction or deflected by an uneven surface. When a fluid is flowing turbulently, it flows in eddies and whirls (or vortices), with more "drag" than when the flow is laminar. Many references are available for assisting in determining when fluid flow is laminar or turbulent (e.g., *Turbulent Flow Analysis: Measurement and Prediction,* P. S. Bernard & J. M. Wallace, John Wiley & Sons, Inc., (2000); *An Introduction to Turbulent Flow,* Jean Mathieu & Julian Scott, Cambridge University Press (2001)).

As used herein, the term "gas chromatography" or "GC" refers to chromatography in which the sample mixture is vaporized and injected into a stream of carrier gas (as nitrogen or helium) moving through a column containing a stationary phase composed of a liquid or a particulate solid and is separated into its component compounds according to the affinity of the compounds for the stationary phase.

As used herein, the term "large particle column" or "extraction column" refers to a chromatography column containing an average particle diameter greater than about 50 μm. As used in this context, the term "about" means±10%.

As used herein, the term "analytical column" refers to a chromatography column having sufficient chromatographic plates to effect a separation of materials in a sample that elute from the column sufficient to allow a determination of the presence or amount of an analyte. Such columns are often distinguished from "extraction columns," which have the general purpose of separating or extracting retained material from non-retained materials in order to obtain a purified sample for further analysis. As used in this context, the term "about" means±10%. In some preferred embodiments, the analytical column contains particles between about 1.5 µm and 3.5 µm in diameter.

As used herein, the term "on-line" or "inline," for example as used in "on-line automated fashion" or "on-line extraction," refers to a procedure performed without the need for operator intervention. In contrast, the term "off-line" as used herein refers to a procedure requiring manual intervention of an operator. Thus, if samples are subjected to precipitation, and the supernatants are then manually loaded into an autosampler, the precipitation and loading steps are off-line from the subsequent steps. In various embodiments of the methods, one or more steps may be performed in an on-line automated fashion.

As used herein, the term "sample injection" refers to introducing an aliquot of a single sample into an analytical instrument, for example a mass spectrometer. This introduction may occur directly or indirectly. An indirect sample injection may be accomplished, for example, by injecting an aliquot of a sample into a HPLC or UPLC analytical column that is connected to a mass spectrometer in an on-line fashion.

As used herein, the term "same sample injection" with respect to multiple analyte analysis by mass spectrometry means that the ions for two or more different analytes are determined essentially simultaneously by measuring ions for the different analytes from the same (i.e. identical) sample injection.

As used herein, the term "mass spectrometry" or "MS" refers to an analytical technique to identify compounds by their mass. MS refers to methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrographic instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., *Prostate Cancer and Prostatic Diseases* 1999, 2: 264-76; and Merchant and Weinberger, *Electrophoresis* 2000, 21: 1164-67.

As used herein, the term "operating in negative ion mode" refers to those mass spectrometry methods where negative ions are generated and detected. The term "operating in positive ion mode" as used herein, refers to those mass spectrometry methods where positive ions are generated and detected.

As used herein, the term "ionization" or "ionizing" refers to the process of generating an analyte ion having a net electrical charge equal to one or more electron units. Negative ions are those having a net negative charge of one or more electron units, while positive ions are those having a net positive charge of one or more electron units.

As used herein, the term "electron ionization" or "EI" refers to methods in which an analyte of interest in a gaseous or vapor phase interacts with a flow of electrons. Impact of the electrons with the analyte produces analyte ions, which may then be subjected to a mass spectrometry technique.

As used herein, the term "chemical ionization" or "CI" refers to methods in which a reagent gas (e.g. ammonia) is subjected to electron impact, and analyte ions are formed by the interaction of reagent gas ions and analyte molecules.

As used herein, the term "fast atom bombardment" or "FAB" refers to methods in which a beam of high energy atoms (often Xe or Ar) impacts a non-volatile sample, desorbing and ionizing molecules contained in the sample. Test samples are dissolved in a viscous liquid matrix such as glycerol, thioglycerol, m-nitrobenzyl alcohol, 18-crown-6 crown ether, 2-nitrophenyloctyl ether, sulfolane, diethanolamine, and triethanolamine. The choice of an appropriate matrix for a compound or sample is an empirical process.

As used herein, the term "matrix-assisted laser desorption ionization" or "MALDI" refers to methods in which a non-volatile sample is exposed to laser irradiation, which desorbs and ionizes analytes in the sample by various ionization pathways, including photo-ionization, protonation, deprotonation, and cluster decay. For MALDI, the sample is mixed with an energy-absorbing matrix, which facilitates desorption of analyte molecules.

As used herein, the term "surface enhanced laser desorption ionization" or "SELDI" refers to another method in which a non-volatile sample is exposed to laser irradiation, which desorbs and ionizes analytes in the sample by various ionization pathways, including photo-ionization, protonation, deprotonation, and cluster decay. For SELDI, the sample is typically bound to a surface that preferentially retains one or more analytes of interest. As in MALDI, this process may also employ an energy-absorbing material to facilitate ionization.

As used herein, the term "electrospray ionization" or "ESI," refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber, which is heated slightly to prevent condensation and to evaporate solvent. As the droplets get smaller the electrical surface charge density increases until such time that the natural repulsion between like charges causes ions as well as neutral molecules to be released.

As used herein, the term "atmospheric pressure chemical ionization" or "APCI," refers to mass spectrometry methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated $N_2$ gas may be used to improve removal of solvent. The gas-phase ionization in APCI can be more effective than ESI for analyzing less-polar species.

The term "atmospheric pressure photoionization" or "APPI" as used herein refers to the form of mass spectrometry where the mechanism for the photoionization of molecule M is photon absorption and electron ejection to form the molecular ion M+. Because the photon energy typically is just above the ionization potential, the molecular ion is less susceptible to dissociation. In many cases it may be possible to analyze samples without the need for chromatography, thus saving significant time and expense. In the presence of water vapor or protic solvents, the molecular ion can extract H to form MH+. This tends to occur if M has a high proton affinity. This does not affect quantitation accuracy because the sum of M+ and MH+ is constant. Drug compounds in protic solvents are usually observed as MH+, whereas nonpolar compounds such as naphthalene or testosterone usually form M+. See, e.g., Robb et al., *Anal. Chem.* 2000, 72(15): 3653-3659.

As used herein, the term "inductively coupled plasma" or "ICP" refers to methods in which a sample interacts with a partially ionized gas at a sufficiently high temperature such that most elements are atomized and ionized.

As used herein, the term "field desorption" refers to methods in which a non-volatile test sample is placed on an ionization surface, and an intense electric field is used to generate analyte ions.

As used herein, the term "desorption" refers to the removal of an analyte from a surface and/or the entry of an analyte into a gaseous phase. Laser desorption thermal desorption is a technique wherein a sample containing the analyte is thermally desorbed into the gas phase by a laser pulse. The laser hits the back of a specially made 96-well plate with a metal base. The laser pulse heats the base and the heats causes the sample to transfer into the gas phase. The gas phase sample is then drawn into the mass spectrometer.

As used herein, the term "selective ion monitoring" is a detection mode for a mass spectrometric instrument in which only ions within a relatively narrow mass range, typically about one mass unit, are detected.

As used herein, "multiple reaction mode," sometimes known as "selected reaction monitoring," is a detection mode for a mass spectrometric instrument in which a precursor ion and one or more fragment ions are selectively detected.

As used herein, an "amount" of an analyte in a body fluid sample refers generally to an absolute value reflecting the mass of the analyte detectable in volume of sample. However, an amount also contemplates a relative amount in comparison to another analyte amount. For example, an amount of an analyte in a sample can be an amount which is greater than a control or normal level of the analyte normally present in the sample.

The term "about" as used herein in reference to quantitative measurements not including the measurement of the mass of an ion, refers to the indicated value plus or minus 10%. Mass spectrometry instruments can vary slightly in determining the mass of a given analyte. The term "about" in the context of the mass of an ion or the mass/charge ratio of an ion refers to +/−0.50 atomic mass unit.

The summary of the invention described above is non-limiting and other features and advantages of the invention will be apparent from the following detailed description of the invention, and from the claims.

DETAILED DESCRIPTION OF THE INVENTION

Figure 1:
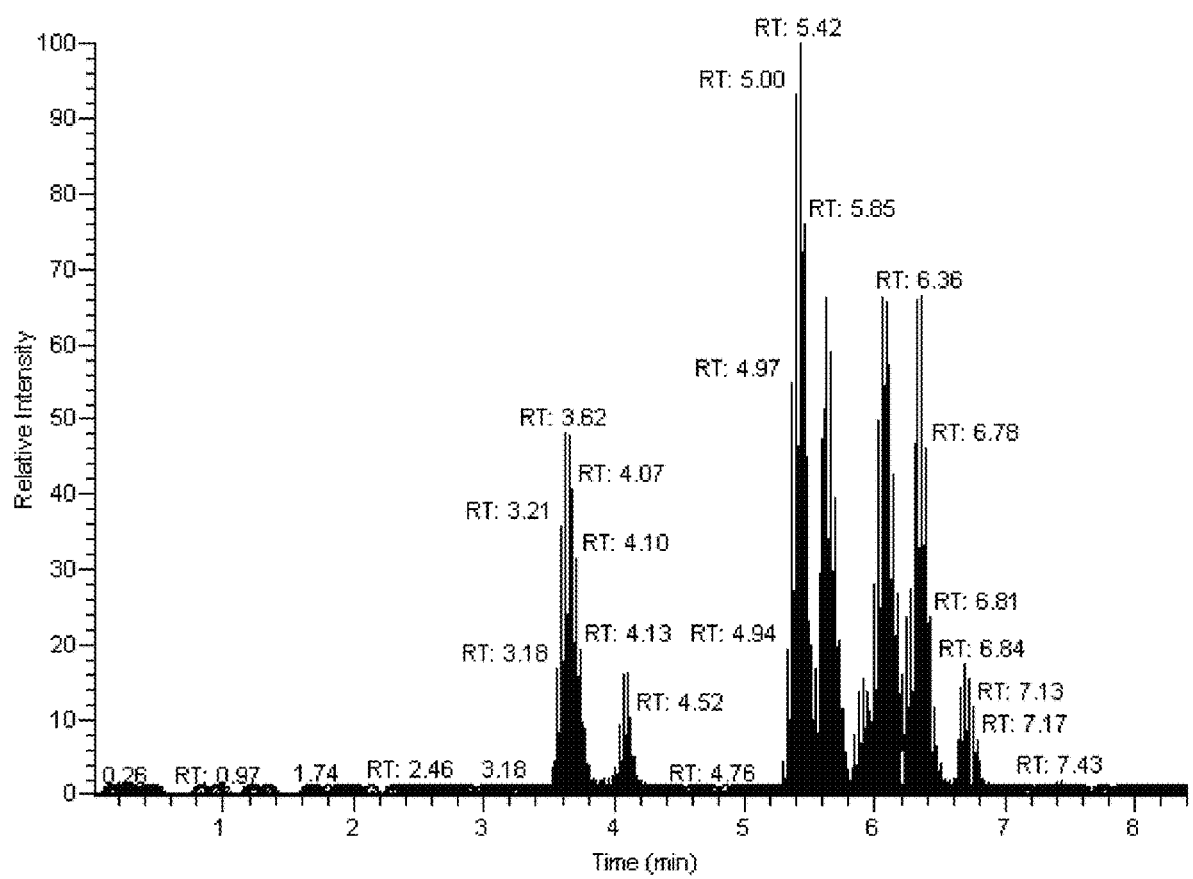
FIG. 1 shows a plot of Total Ion Count for a single sample injection containing thirteen HRT panel analytes. Details are discussed in Example 4.

Methods are described for measuring the amount of one or more HRT panel analytes in a sample. More specifically, mass spectrometric methods are described for quantifying one or more HRT panel analytes in a sample that typically has been purified by one or more steps prior to mass spectrometry. The methods may utilize a liquid chromatography step such as turbulent flow liquid chromatography (TFLC) to perform a purification of selected analytes combined with methods of mass spectrometry (MS) thereby providing a high-throughput assay system for quantifying one or more HRT panel analytes in a sample. The preferred embodiments are particularly well suited for application in large clinical laboratories for automated HRT monitoring.

Suitable samples for use in methods of the present invention include any sample that may contain one or more of the analytes of interest. In some preferred embodiments, a sample is a biological sample; that is, a sample obtained from any biological source, such as an animal, a cell culture, an organ culture, etc. In certain preferred embodiments, samples are obtained from a mammalian animal, such as a dog, cat, horse, etc. Particularly preferred mammalian animals are primates, most preferably male or female humans. Preferred samples comprise bodily fluids such as urine, blood, plasma, serum, saliva, and cerebrospinal fluid, or tissue samples; preferably plasma or serum; most preferably serum. Such samples may be obtained, for example, from a patient; that is, a living person, male or female, presenting oneself in a clinical setting for diagnosis, prognosis, or treatment of a disease or condition. The sample is preferably obtained from a patient, for example, blood serum.

When evaluating the result of analysis of a patient sample, a ratio may be calculated comparing the amount of one or more sulfated analyte to one or more un-sulfated analyte. In preferred embodiments, the sulfated and un-sulfated analytes comprise sulfated and un-sulfated forms of the same analyte (for example, estrone sulfate:estrone). However, the number type of sulfated analytes utilized need not be the same as the number and type of un-sulfated analytes utilized when determining the ratio.

A predominance of non-sulfated analytes may indicate that a decrease in the individual's HRT dosage may be desirable. Alternatively, if sulfated analytes are predominant, an increase in the individual's HRT dosage may be desirable.

The present invention also contemplates kits for a HRT monitoring assay. A kit for a HRT monitoring assay may include a kit comprising the compositions provided herein. For example, a kit may include packaging material and measured amounts of one or more isotopically labeled internal standard, in amounts sufficient for at least one assay. Typically, the kits will also include instructions recorded in a tangible form (e.g., contained on paper or an electronic medium) for using the packaged reagents for use in a HRT monitoring assay.

Sample Preparation for Mass Spectrometry

Some or all HRT panel analytes in a sample may be bound to proteins, such as sex hormone binding globulin (SHBG) or albumin, if present in the sample. Various methods may be used to disrupt the interaction between HRT panel analytes and protein prior to the implementation of one or more enrichment steps and/or MS analysis so that the amount of a HRT panel analyte measured by mass spectrometry is a reflection of the total for that HRT panel analyte in the sample (e.g., free estradiol and estradiol bound to protein). Once HRT panel analytes and proteins have been separated in the sample, HRT panel analytes may be enriched relative to one or more other components in the sample (e.g. protein) by various methods known in the art, such as for example, liquid chromatography, filtration, centrifugation, thin layer chromatography (TLC), electrophoresis including capillary electrophoresis, affinity separations including immunoaffinity separations, extraction methods including ethyl acetate or methanol extraction, and the use of chaotropic agents or any combination of the above or the like.

Protein precipitation is one preferred method of preparing a sample, especially a biological sample, such as serum or plasma. Such protein purification methods are well known in the art, for example, Polson et al., *Journal of Chromatography B* 785:263-275 (2003), describes protein precipitation techniques suitable for use in the methods. Protein precipitation may be used to remove most of the protein from the sample leaving HRT panel analytes in the supernatant. The samples may be centrifuged to separate the liquid supernatant from the precipitated proteins. The resultant supernatant may then be applied to liquid chromatography and subsequent mass spectrometry analysis. In certain embodiments, the use of protein precipitation such as for example, acetonitrile protein precipitation, obviates the need for turbulent flow liquid chromatography (TFLC) or other on-line extraction prior to HPLC and mass spectrometry. Accordingly in such embodiments, the method involves (1) performing a protein precipitation of the sample of interest; and (2) loading the supernatant directly onto the HPLC-mass spectrometer without using on-line extraction or turbulent flow liquid chromatography (TFLC).

In other preferred embodiments, HRT panel analytes may be released from a protein without having to precipitate the protein. For example, an aqueous formic acid solution may be added to the sample to disrupt interaction between a protein and a HRT panel analyte. Alternatively, ammonium sulfate may be added to the sample to disrupt ionic interactions between a carrier protein and a HRT panel analyte without precipitating the carrier protein.

In some preferred embodiments, TFLC, alone or in combination with one or more purification methods, may be used to purify HRT panel analytes prior to mass spectrometry. In such embodiments HRT panel analytes may be extracted using an TFLC extraction cartridge which captures the analytes, then eluted and chromatographed on a second TFLC column or onto an HPLC or UPLC analytical column prior to ionization. Because the steps involved in these chromatography procedures can be linked in an automated fashion, the requirement for operator involvement during the purification of the analyte can be minimized. This feature can result in savings of time and costs, and eliminate the opportunity for operator error.

It is believed that turbulent flow, such as that provided by TFLC columns and methods, may enhance the rate of mass transfer, improving separation characteristics. TFLC columns separate components by means of high chromatographic flow rates through a packed column containing rigid particles. By employing high flow rates (e.g., 3-5 mL/min), turbulent flow occurs in the column that causes nearly complete interaction between the stationary phase and the analyte(s) of interest. An advantage of using TFLC columns is that the macromolecular build-up associated with biological fluid matrices is avoided since the high molecular weight species are not retained under the turbulent flow conditions. TFLC methods that combine multiple separations in one procedure lessen the need for lengthy sample preparation and operate at a significantly greater speed. Such methods also achieve a separation performance superior to laminar flow (HPLC) chromatography. TFLC often allows for direct injection of biological samples (plasma, urine, etc.). Direct injection is difficult to achieve in traditional forms of chromatography because denatured proteins and other biological debris quickly block the separation columns. TFLC also allows for very low sample volume of less than 1 mL, preferably less than 0.5 mL, preferably less than 0.2 mL, preferably about 0.1 mL.

Examples of TFLC applied to sample preparation prior to analysis by mass spectrometry have been described elsewhere. See, e.g., Zimmer et al., *J. Chromatogr. A* 854:23-35 (1999); see also, U.S. Pat. Nos. 5,968,367; 5,919,368; 5,795,469; and 5,772,874. In certain embodiments of the method, samples are subjected to protein precipitation as described above prior to loading on the TFLC column; in alternative preferred embodiments, the samples may be loaded directly onto the TFLC without being subjected to protein precipitation. Preferably, TFLC is used in conjunction with HPLC to extract and purify one or more HRT panel analytes without subjecting the sample to protein precipitation. In related preferred embodiments, purifying the sample prior to MS analysis involves (i) applying the sample to a TFLC extraction column, (ii) washing the TFLC extraction column under conditions whereby one or more HRT panel analytes are retained by the column, (iii) eluting retained HRT panel analytes from the TFLC extraction column, (iv) applying the retained material to an analytical column, and (v) eluting purified HRT panel analytes from the analytical column. The TFLC extraction column is preferably a large particle column. In various embodiments, one of more steps of the methods may be performed in an on-line, automated fashion. For example, in one embodiment, steps (i)-(v) are performed in an on-line, automated fashion. In another, the steps of ionization and detection are performed on-line following steps (i)-(v).

One means of sample purification that may be used prior to mass spectrometry is liquid chromatography (LC). Certain LC techniques, including HPLC, rely on relatively slow, laminar flow technology. Traditional HPLC analysis relies on column packings in which laminar flow of the sample through the column is the basis for separation of the analyte of interest from the sample. The skilled artisan will understand that separation in such columns is a diffusional process and may select HPLC instruments and columns that are suitable for use with HRT panel analytes. The chromatographic column typically includes a medium (i.e., a packing material) to facilitate separation of chemical moieties (i.e., fractionation). The medium may include minute particles. The particles include a bonded surface that interacts with the various chemical moieties to facilitate separation of the chemical moieties. One suitable bonded surface is a hydrophobic bonded surface such as an alkyl bonded surface. Alkyl bonded surfaces may include C-4, C-8, C-12, or C-18 bonded alkyl groups, preferably C-18 bonded groups. The chromatographic column includes an inlet port for receiving a sample directly or indirectly from a solid-phase extraction or TFLC column and an outlet port for discharging an effluent that includes the fractionated sample.

In one embodiment, the sample is applied to the column at the inlet port, eluted with a solvent or solvent mixture, and discharged at the outlet port. Different solvent modes may be selected for eluting the analyte(s) of interest. For example, liquid chromatography may be performed using a gradient mode, an isocratic mode, or a polytyptic (i.e. mixed) mode. During chromatography, the separation of materials is effected by variables such as choice of eluent (also known as a "mobile phase"), elution mode, gradient conditions, temperature, etc.

In certain embodiments, an analyte may be purified by applying a sample to a column under conditions where the analyte of interest is reversibly retained by the column packing material, while one or more other materials are not retained. In these embodiments, a first mobile phase condition can be employed where the analyte of interest is retained by the column, and a second mobile phase condition can subsequently be employed to remove retained material from the column, once the non-retained materials are washed through. Alternatively, an analyte may be purified by applying a sample to a column under mobile phase conditions where the analyte of interest elutes at a differential rate in comparison to one or more other materials. Such procedures may enrich the amount of one or more analytes of interest relative to one or more other components of the sample.

In one preferred embodiment, HPLC is conducted on a hydrophobic column chromatographic system. In certain preferred embodiments, a C18 analytical column is used (e.g., an XBridge C18 column from Waters, Corp. (3.5 µm particle size; 100×3.0 mm), a Hypersil Gold column from ThermoFisher (3 µm particle size; 100×3.0 mm), or equivalent). In certain preferred embodiments, TFLC and HPLC are performed using HPLC Grade Ultra Pure water and 100% methanol as mobile phases.

By careful selection of valves and connector plumbing, two or more chromatography columns may be connected as needed such that material is passed from one to the next without the need for any manual steps. In preferred embodiments, the selection of valves and plumbing is controlled by a computer pre-programmed to perform the necessary steps. Most preferably, the chromatography system is also connected in such an on-line fashion to the detector system, e.g., an MS system. Thus, an operator may place a tray of samples in an autosampler, and the remaining operations are performed under computer control, resulting in purification and analysis of all samples selected.

In some embodiments, TFLC may be used for purification of one or more HRT panel analytes prior to mass spectrometry. In such embodiments, one or more HRT panel analytes may be extracted using a TFLC extraction column, then eluted and chromatographed on a second TFLC column or onto an analytical HPLC column prior to ionization. For example, HRT panel analyte extraction with an TFLC extraction column may be accomplished with a large particle size (50 µm) packed column. Sample eluted off of this column may then be transferred to an HPLC analytical column for further purification prior to mass spectrometry. In preferred embodiments, a large particle polymer based column, such as a Cyclone P® column from Cohesive Technologies, Inc. (50 µm particle size, 1.0×50 mm), or equivalent is used as the TFLC column. Because the steps involved in these chromatography procedures may be linked in an automated fashion, the requirement for operator involvement during the purification of the analyte can be minimized. This feature may result in savings of time and costs, and eliminate the opportunity for operator error.

Detection and Quantitation by Mass Spectrometry

In various embodiments, one or more HRT panel analytes may be ionized by any method known to the skilled artisan. Mass spectrometry is performed using a mass spectrometer, which includes an ion source for ionizing the fractionated sample and creating charged molecules for further analysis. For example ionization of the sample may be performed by electron ionization, chemical ionization, electrospray ionization (ESI), photon ionization, atmospheric pressure chemical ionization (APCI), photoionization, atmospheric pressure photoionization (APPI), fast atom bombardment (FAB), liquid secondary ionization (LSI), matrix assisted laser desorption ionization (MALDI), field ionization, field desorption, thermospray/plasmaspray ionization, surface enhanced laser desorption ionization (SELDI), inductively coupled plasma (ICP) and particle beam ionization. The skilled artisan will understand that the choice of ionization method may be determined based on the analyte to be measured, type of sample, the type of detector, the choice of positive versus negative mode, etc.

The one or more HRT panel analytes may be ionized in positive or negative mode to create one or more HRT panel ions. In preferred embodiments, the one or more HRT panel analytes are ionized by electrospray ionization (ESI) in positive or negative mode; preferably negative mode. In alternative preferred embodiments, the one or more HRT panel analytes are ionized by atmospheric pressure chemical ionization (APCI) in positive or negative mode; preferably negative mode. In related preferred embodiments, the one or more HRT panel ions are in a gaseous state and the inert collision gas is argon or nitrogen.

In mass spectrometry techniques generally, after the sample has been ionized, the positively or negatively charged ions thereby created may be analyzed to determine a mass-to-charge ratio. Suitable analyzers for determining mass-to-charge ratios include quadrupole analyzers, ion traps analyzers, and time-of-flight analyzers. Exemplary ion trap methods are described in Bartolucci, et al., *Rapid Commun. Mass Spectrom.* 2000, 14:967-73.

The ions may be detected using several detection modes. For example, selected ions may be detected, i.e. using a selective ion monitoring mode (SIM), or alternatively, ions may be detected using a scanning mode, e.g., multiple reaction monitoring (MRM) or selected reaction monitoring (SRM). Preferably, the mass-to-charge ratio is determined using a quadrupole analyzer. For example, in a "quadrupole" or "quadrupole ion trap" instrument, ions in an oscillating radio frequency field experience a force proportional to the DC potential applied between electrodes, the amplitude of the RF signal, and the mass/charge ratio. The voltage and amplitude may be selected so that only ions having a particular mass/charge ratio travel the length of the quadrupole, while all other ions are deflected. Thus, quadrupole instruments may act as both a "mass filter" and as a "mass detector" for the ions injected into the instrument.

One may enhance the resolution of the MS technique by employing "tandem mass spectrometry," or "MS/MS". In this technique, a precursor ion (also called a parent ion) generated from a molecule of interest can be filtered in an MS instrument, and the precursor ion subsequently fragmented to yield one or more fragment ions (also called daughter ions or product ions) that are then analyzed in a second MS procedure. By careful selection of precursor ions, only ions produced by certain analytes are passed to the fragmentation chamber, where collisions with atoms of an inert gas produce the fragment ions. Because both the precursor and fragment ions are produced in a reproducible fashion under a given set of ionization/fragmentation conditions, the MS/MS technique may provide an extremely powerful analytical tool. For example, the combination of filtration/fragmentation may be used to eliminate interfering substances, and may be particularly useful in complex samples, such as biological samples.

The mass spectrometer typically provides the user with an ion scan; that is, the relative abundance of each ion with a particular mass/charge over a given range (e.g., 100 to 1000 amu). The results of an analyte assay, that is, a mass spectrum, may be related to the amount of the analyte in the original sample by numerous methods known in the art. For example, given that sampling and analysis parameters are carefully controlled, the relative abundance of a given ion may be compared to a table that converts that relative abundance to an absolute amount of the original molecule. Alternatively, external standards may be run with the samples, and a standard curve constructed based on ions generated from those standards. Using such a standard curve, the relative abundance of a given ion may be converted into an absolute amount of the original molecule. In certain preferred embodiments, an internal standard is used to generate a standard curve for calculating the quantity of one or more HRT panel analytes. Methods of generating and using such standard curves are well known in the art and one of ordinary skill is capable of selecting an appropriate internal standard. For example, in preferred embodiments one or more isotopically labeled analogues of HRT panel analytes (e.g., $d_4$-estrone (E1-d4), $d_2$-17α-estradiol (E2a-d2), $d_5$-17β-estradiol (E2b-d5), $d_3$-estriol (E3-d3), $d_4$-equilin (EQ-d4), $d_5$-17β-dihydroequilin (EQb-d5), $d_3$-equilenin (EN-d3), $d_3$-17β-dihydroequilenin (ENb-d3), $d_4$-estrone sulfate (E1s-d4), $d_4$-17β-estradiol sulfate (E2bs-d4), and $d_2$-Δ8,9-dehydroestrone (dE1-d2)) may be used as internal standards. Numerous other methods for relating the amount of an ion to the amount of the original molecule will be well known to those of ordinary skill in the art.

One or more steps of the methods may be performed using automated machines. In certain embodiments, one or more purification steps are performed on-line, and more preferably all of the purification and mass spectrometry steps may be performed in an on-line fashion.

In certain embodiments, such as MS/MS, where precursor ions are isolated for further fragmentation, collision activation dissociation (CAD) is often used to generate fragment ions for further detection. In CAD, precursor ions gain energy through collisions with an inert gas, and subsequently fragment by a process referred to as "unimolecular decomposition." Sufficient energy must be deposited in the precursor ion so that certain bonds within the ion can be broken due to increased vibrational energy.

In particularly preferred embodiments, one or more HRT panel analytes are quantified in a sample using MS/MS as follows. The samples are subjected to liquid chromatography, preferably TFLC followed by HPLC; the flow of liquid solvent from the chromatographic column enters the heated nebulizer interface of an MS/MS analyzer; and the solvent/analyte mixture is converted to vapor in the heated tubing of the interface. The HRT analytes contained in the nebulized solvent are then ionized. The ions, e.g. precursor ions, pass through the orifice of the instrument and enter the first quadrupole. Quadrupoles 1 and 3 (Q1 and Q3) are mass filters, allowing selection of ions (i.e., selection of "precursor" and "fragment" ions in Q1 and Q3, respectively) based on their mass to charge ratio (m/z). Quadrupole 2 (Q2) is the collision cell, where ions are fragmented. The first quadrupole of the mass spectrometer (Q1) selects for molecules with the mass to charge ratios of one of the HRT panel analytes. Precursor ions with the correct mass/charge ratios are allowed to pass into the collision chamber (Q2), while unwanted ions with any other mass/charge ratio collide with the sides of the quadrupole and are eliminated. Precursor ions entering Q2 collide with neutral collision gas molecules and fragment. The fragment ions generated are passed into quadrupole 3 (Q3), where the fragment ions of the selected HRT panel analyte are selected while other ions are eliminated. During analysis of a single sample injection, Q1 and/or Q3 may be adjusted such that mass/charge ratios of one or more precursor ion/fragment ion pairs specific to one HRT panel analyte are first selected, followed at some later time by the selection of mass/charge ratios of one or more precursor ion/fragment ion pairs specific to a second HRT panel analyte, optionally repeated at some later time for as many HRT panel analytes as is desired. In particularly preferred embodiments, at least one precursor ion/fragment ion pair is selected for every HRT panel analyte in an analysis of a single sample injection, although the sequence of pair selection may occur in any order.

The methods may involve MS/MS performed in either positive or negative ion mode; preferably negative ion mode. Using standard methods well known in the art, one of ordinary skill is capable of identifying one or more fragment ions of a particular precursor ion of a HRT panel analyte that may be used for selection in quadrupole 3 (Q3). Preferred precursor ion/fragment ions for HRT panel analytes and exemplary internal standards are found in Table 1.

TABLE 1

Preferred Precursor Ion/Fragment Ion Mass to Charge Ratios of HRT Panel Analytes and Exemplary Internal Standards

| Analyte | Abbr. | Parent (m/z) | Fragment(s) (m/z) |
|---|---|---|---|
| Equilenin | EN | 265.09 | 193.10, 221.08 |
| 17α-Dihydroequilenin | ENa | 267.08 | 180.10, 195.13 |
| 17β-Dihydroequilenin | ENb | 267.08 | 180.09, 195.12 |
| Equilin | EQ | 267.06 | 115.07, 181.07 |
| Δ8,9-Dehydroestrone | dE1 | 267.06 | 171.07, 195.08 |
| $d_3$-Equilenin | EN-d3 | 268.15 | 182.08 |
| 17β-Dihydroequilin | EQb | 269.09 | 143.10, 193.10 |
| Estrone | E1 | 269.10 | 143.09, 145.10 |
| 17α-Dihydroequilin | EQa | 269.10 | 169.10, 183.11 |
| $d_3$-17β-Dihydroequilenin | ENb-d3 | 270.17 | 182.08 |
| 17α-Estradiol | E2a | 271.12 | 143.1, 145.10 |
| 17β-Estradiol | E2b | 271.12 | 169.10, 183.10 |
| $d_4$-Equilin | EQ-d4 | 271.16 | 243.14 |
| $d_4$-Estrone | E1-d4 | 273.13 | 147.08 |
| $d_2$-17α-Estradiol | E2a-d2 | 273.20 | 147.08 |
| $d_5$-17β-Dihydroequilin | EQb-d5 | 274.15 | 213.10 |
| $d_5$-17β-Estradiol | E2b-d5 | 276.13 | 187.08 |
| Estriol | E3 | 287.10 | 143.10, 171.10 |
| $d_3$-Estriol | E3-d3 | 290.20 | 173.10 |
| Estrone Sulfate | E1s | 349.01 | 143.08, 145.10 |
| $d_4$-Estrone Sulfate | E1s-d4 | 352.9 | 147.09 |
| Estradiol Sulfate | E2s | 351.02 | 145.10, 183.10 |
| $d_4$-17β-Estradiol Sulfate | E2bs-d4 | 355.0 | 275.18 |
| $d_2$-Δ8,9-Dehydroestrone | dE1-d2 | 269.02 | 209.05 |

In Table 1, above, a plurality of preferred fragment ions are listed for equilenin, 17α-dihydroequilenin, 17β-dihydroequilenin, equilin, Δ8,9-dehydroestrone, 17β-dihydroequilin, estrone, 17α-dihydroequilin, 17α-estradiol, 17β-estradiol, estriol, estrone sulfate, and estradiol sulfate). In alternative embodiments, a single fragment ion may be detected for these HRT panel analytes. For example, a single fragment ion with a m/z of 181.1 may be detected for equilin; a single fragment ion with a m/z of 171.07 may be detected for Δ8,9-dehydroestrone; a single fragment ion with a m/z of 143.10 may be detected for 17β-dihydroequilin; and a single fragment ion with a m/z of 169.10 may be detected for 17α-dihydroequilin.

As ions collide with the detector they produce a pulse of electrons that are converted to a digital signal. The acquired data is relayed to a computer, which plots counts of the ions collected versus time. The resulting mass chromatograms are similar to chromatograms generated in traditional HPLC-MS methods. The areas under the peaks corresponding to particular ions, or the amplitude of such peaks, may be measured and correlated to the amount of the analyte of interest. In certain embodiments, the area under the curves, or amplitude of the peaks, for fragment ion(s) and/or precursor ions are measured to determine the amount of each HRT panel analyte detected. As described above, the relative abundance of a given ion may be converted into an absolute amount of the original analyte using calibration standard curves based on peaks of one or more ions of an internal molecular standard.

The following Examples serve to illustrate the invention. These Examples are in no way intended to limit the scope of the methods.

EXAMPLES

Example 1

Sample Preparation

Blood was collected in a Vacutainer with no additives and allowed to clot 30 minutes at room temperature, 18° to 25° C. Serum was collected for further analysis. Samples that exhibited gross hemolysis and/or lipemia were excluded.

Example 2

Extraction of HRT Panel Analytes from Samples Using TFLC-HPLC

Serum was prepared for LC by pipetting 200 μL of patient serum into a well of a 96-well plate. 25 μL of a combined internal standard solution was added to each well along with 300 μL of 40% ethanol solution. The samples were incubated at room temperature for 30 to 45 minutes prior to LC.

Liquid chromatography was performed on some samples with a Cohesive Technologies Aria TX-4 HTLC system using Aria OS V 1.5 or newer software. An autosampler wash solution was prepared using 30% acetonitrile, 30% methanol, 30% isopropanol, and 10% acetone (v/v).

In one example, the HTLC system automatically injected 75 μL of an above prepared sample into a Cyclone P® extraction column from Cohesive Technologies, Inc. (50 μm particle size, 1.0×50 mm). The samples were loaded at a high flow rate to create turbulence inside the extraction column. This turbulence ensured optimized binding of HRT panel analytes to the large particles in the column and the passage of residual protein and debris to waste.

Following loading, the flow direction was reversed and the sample eluted and transferred to either a XBridge C18 analytical column from Waters, Corp. (3.5 μm particle size; 150×3.0 mm) or a Hypersil Gold analytical column from ThermoFisher (3 μm particle size; 100×3.0 mm) in a column oven/heater set at 40°. A binary HPLC gradient was applied to the analytical column to separate HRT panel analytes from each other and other analytes contained in the sample. Mobile phase A was 0.1% aqueous ammonium hydroxide and mobile phase B was 100% methanol. The approximate retention times of the various HRT panel analytes are shown in Table 2.

TABLE 2

Approximate Retention Times of HRT Panel Analytes

| Analyte | Abbr. | Approximate Retention Time |
|---|---|---|
| Estrone Sulfate | E1s | 3.53 |
| Estradiol Sulfate | E2s | 3.53 |
| Estriol | E3 | 4.07 |
| Equilenin | EN | 5.16 |

TABLE 2-continued

Approximate Retention Times of HRT Panel Analytes

| Analyte | Abbr. | Approximate Retention Time |
|---|---|---|
| 17β-Dihydroequilenin | ENb | 5.48 |
| 17α-Dihydroequilenin | ENa | 5.88 |
| 17β-Dihydroequilin | EQb | 6.00 |
| Δ8,9-Dehydroestrone | dE1 | 6.16 |
| Equilin | EQ | 6.18 |
| 17α-Dihydroequilin | EQa | 6.20 |
| 17β-Estradiol | E2b | 6.31 |
| Estrone | E1 | 6.44 |
| 17α-Estradiol | E2a | 6.62 |

These separated samples were then subjected to MS/MS for quantitation of selected HRT panel analytes.

Example 3

Extraction of HRT Panel Analytes from Samples Using TFLC-UPLC

Processed serum samples were alternatively subject to TFLC-UPLC, rather than TFLC-HPLC extraction as described above. In this instance, the HTLC system automatically injected 75 μL of an above processed serum into a Cyclone P® extraction column from Cohesive Technologies, Inc. (50 μm particle size, 1.0×50 mm). The samples were loaded at a high flow rate to create turbulence inside the extraction column. This turbulence ensured optimized binding of HRT panel analytes to the large particles in the column and the passage of residual protein and debris to waste.

Following loading, the flow direction was reversed and the sample eluted and transferred to either a Hypersil Gold analytical column from ThermoFisher (1.7 μm particle size; 50×2.1 mm) at 260 bar without heat at 0.45 mL/min, or an Acquity BEH C18 analytical column from Waters (1.7 μm particle size; 50×2.1 mm) at 280 bar with heat set at 40°-50° at 0.5 mL/min. A binary UPLC gradient was applied to the analytical column, to separate HRT panel analytes from each other and other analytes contained in the sample. Mobile phase A was Ultra Pure Water (HPLC grade) and mobile phase B was 100% methanol.

These separated samples were then subjected to mass spectrometric analysis for quantitation of selected HRT panel analytes.

Example 4

Quantitation of HRT Panel Analytes by MS/MS

MS (and MS/MS) was performed using a Thermo TSQ Quantum Ultra MS/MS system. The following software programs all from ThermoElectron were used in the Examples described herein: Tune Master V 1.5 or newer, Xcalibur V 2.0.7 SR1 or newer, TSQ Quantum 1.5 or newer, LCQuan V 2.5.6 or newer, and XReport 1.0 or newer. The solvent/analyte mixture was converted to vapor in the heated tubing of the interface. Analytes in the nebulized solvent were ionized by heated ESI.

First, a Total Ion Count was measured for a single sample injection containing thirteen HRT panel analytes. This scan is shown in FIG. 1 and demonstrates the total ion count versus time.

Then MS/MS analysis was conducted by passing ions to the first quadrupole (Q1), which selected ions with a desired parent mass to charge ratio. Ions entering quadrupole 2 (Q2) collided with argon gas to generate ion fragments, which were passed to quadrupole 3 (Q3) for further selection. Simultaneously, the same process using isotope dilution mass spectrometry was carried out with selected isotope-labeled internal standards. All of the selected masses for each HRT panel analyte and selected isotope-labeled internal standards are listed in Table 1, above.

Figure 2:
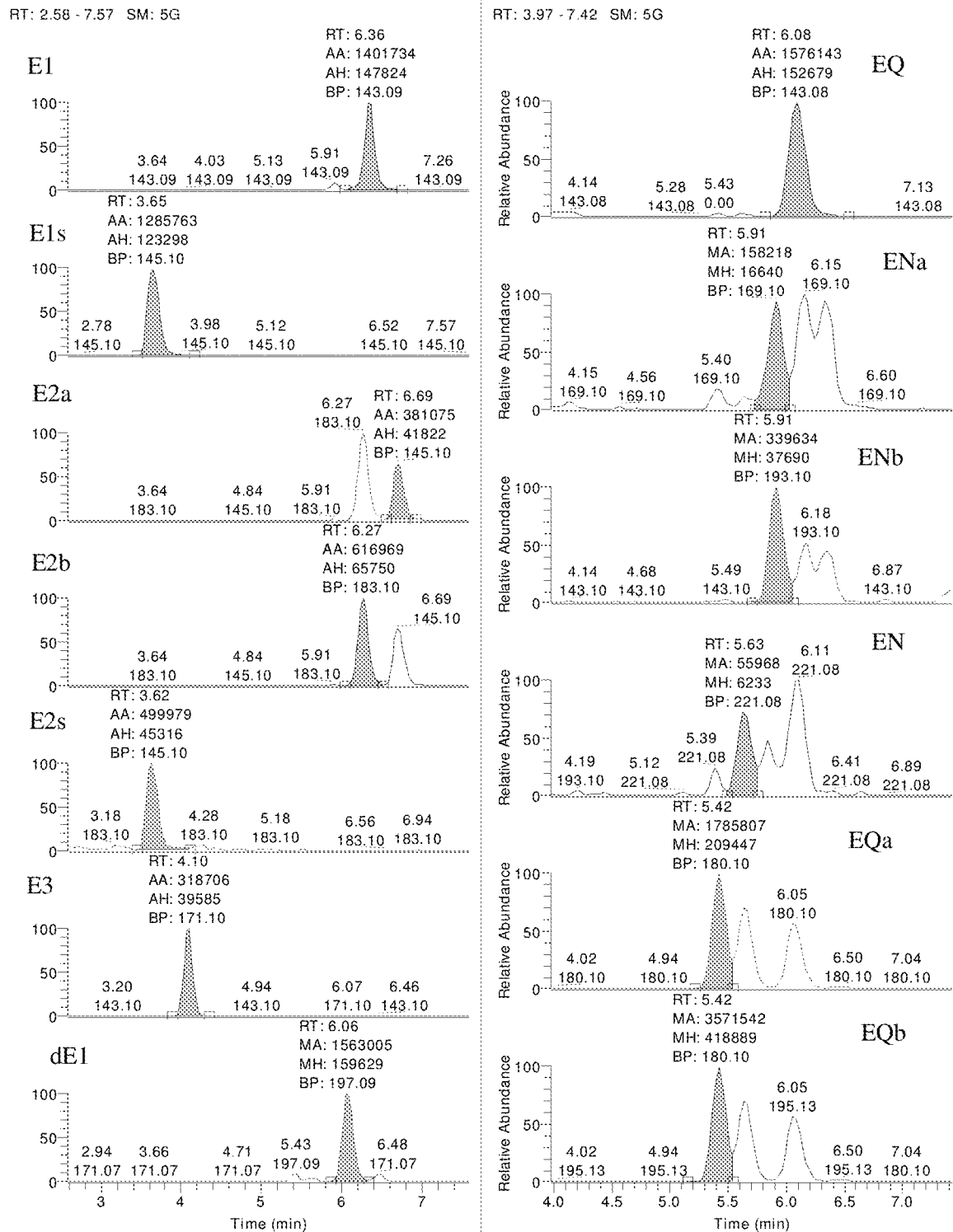
FIG. 2 shows HRT panel analyte peaks generated by TFLC followed by HPLC-MS/MS. Details are described in Example 4.

FIG. 2 shows the results of monitoring the mass transitions listed in Table 1 for HRT panel analytes in a single sample injection. As seen in this Figure, all 13 analytes were detected in a single sample injection.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

That which is claimed is:

1. A method for simultaneous quantitation of a panel of estrogenic compounds in an individual undergoing hormone replacement therapy (HRT), the method comprising:
   a. purifying a sample from an individual undergoing HRT by liquid chromatography;
   b. ionizing the sample by atmospheric pressure chemical ionization (APCI) in negative ion mode to produce one or more precursor ions of each of estrogenic compounds in a panel, wherein the panel comprises estrone (E1), 17β-estradiol (E2b), estrone sulfate (E1s), 17α-estradiol (E2a), estradiol sulfate (E2s), estriol (E3), equilin (EQ), 17α-dihydroequilin (EQa), 17β-dihydroequilin (EQb), equilenin (EN), 17α-dihydroequilenin (ENa), 17β-dihydroequilenin (ENb), and Δ8,9-dehydroestrone (dE1);
   c. fragmenting the precursor ions to one or more fragment ions of each of said estrogenic compounds, wherein said fragment ions are detectable by mass spectrometry;
   d. determining the amounts of one or more fragment ions of each of said estrogenic compounds by tandem mass spectrometry; wherein the amounts of one or more fragment ions is used to determine the amounts of each of estrogenic compounds in the sample of the individual.

2. The method of claim 1, wherein the liquid chromatography is selected from the group consisting of high performance liquid chromatography, ultra high performance liquid chromatography, and turbulent flow liquid chromatography.

3. The method of claim 1, wherein the sample comprises serum or plasma.

4. The method of claim 1, further comprising determining the amount of one or more internal standards by tandem mass spectrometry.

5. The method of claim 4, wherein the internal standard comprises an isotopically labeled internal standard.

\* \* \* \* \*